US008417538B2

(12) United States Patent
Tessier

(10) Patent No.: US 8,417,538 B2
(45) Date of Patent: *Apr. 9, 2013

(54) SYSTEM AND METHOD FOR PERFORMING OBJECT ASSOCIATION BASED ON INTERACTION TIME USING A LOCATION TRACKING SYSTEM

(75) Inventor: Paul Tessier, Lynnfield, MA (US)

(73) Assignee: Consortium P, Inc., Rochester, NH (US)

( * ) Notice: Subject to any disclaimer, the term of this patent is extended or adjusted under 35 U.S.C. 154(b) by 1102 days.

This patent is subject to a terminal disclaimer.

(21) Appl. No.: 12/024,711

(22) Filed: Feb. 1, 2008

(65) Prior Publication Data

US 2009/0198734 A1    Aug. 6, 2009

Related U.S. Application Data

(63) Continuation-in-part of application No. 11/503,651, filed on Aug. 14, 2006, now abandoned, which is a continuation of application No. 10/096,187, filed on Mar. 11, 2002, now Pat. No. 7,099,895.

(60) Provisional application No. 60/274,544, filed on Mar. 9, 2001.

(51) Int. Cl.
*G06Q 10/00* (2012.01)
*G06F 17/30* (2006.01)

(52) U.S. Cl.
USPC .............................................. 705/2; 707/120

(58) Field of Classification Search ....................... 705/2
See application file for complete search history.

(56) References Cited

U.S. PATENT DOCUMENTS

| 5,748,907 A * | 5/1998 | Crane ................................ 705/2 |
| 2003/0155413 A1 | 8/2003 | Kovesdi et al. |
| 2005/0128143 A1* | 6/2005 | Dempsey et al. ............. 342/463 |
| 2006/0229928 A1* | 10/2006 | Nix, Jr. ............................. 705/9 |
| 2007/0013528 A1* | 1/2007 | Kantrowitz et al. ....... 340/573.4 |

OTHER PUBLICATIONS

International Search Report for Application No. PCT/US2009-030848, dated Feb. 23, 2009.

* cited by examiner

*Primary Examiner* — Hiep V Nguyen
(74) *Attorney, Agent, or Firm* — Maine Cernota & Rardin

(57) ABSTRACT

A system is provided for associating an object with a locale or a second object based on interaction time. The system includes and object identifier linked with an object for providing data identifying the object and a location determining module for determining the location of the object. The location determining modules includes an object location module for determining the location of the object based at least in part on the data and an object association module for associating the object with a second object or locale. The object association module is configured to determine whether the object is in proximity to the second object or the locale for a time period greater than or equal to a threshold time and create an associating between the object and the second object or the locale.

35 Claims, 10 Drawing Sheets

SYSTEM AND METHOD FOR PERFORMING OBJECT ASSOCIATION BASED ON INTERACTION TIME USING A LOCATION TRACKING SYSTEM

REFERENCE TO RELATED APPLICATIONS

This application is a continuation-in-part of and claims priority to U.S. patent application Ser. No. 11/503,651, filing date Aug. 14, 2006 now abandoned, which is a continuation patent application of U.S. patent application Ser. No. 10/096,187, filing date Mar. 11, 2002, which claims priority to U.S. provisional application No. 60/274,544, filing date Mar. 9, 2001; U.S. patent application Ser. No. 10/096,187 issued as U.S. Pat. No. 7,099,895 on Aug. 29, 2006. The contents of the aforementioned applications and patents are incorporated herein by reference.

FIELD OF THE INVENTION

The illustrative embodiment of the present invention relates generally to a location tracking system and more particularly to performing associations of objects, people and locations based on interaction time using a location tracking system.

BACKGROUND

There is a need to automatically and accurately track the amount of time a person or object spends interacting or associating with other people or objects. This association information may be used for accounting purposes, for worker payroll, to bill a customer, or to log the "work expended" on a given object or by a given person. Alternatively, the information may be used for inventory records, equipment utilization studies, event precipitation and similar uses. Unfortunately, the accuracy of today's object association systems is inadequate. Conventional object association systems require estimates to capture the amount of time devices spend interacting. For example, it is quite common to estimate the amount of time that an expensive piece of medical equipment was used during a procedure. Since medical equipment can generate millions of dollars a year in bills corresponding to the time the equipment is operated, a small inaccuracy in estimation of the time of operation has a big impact on either the payer or the payee. Accordingly, it is becoming more common for medical insurance companies to demand exact time recordings of the usage of particular equipment. Since this requires human oversight, the process becomes overly burdensome for the medical staff.

The need for humans to initiate conventional object association systems represents a major difficulty with the systems. This requirement for manual interaction, typically to start and stop timers or record times, results in inaccurate readings that can be subject to fraud. Some people simply forget to start or stop the timers, especially when they have multiple tasks to perform, or they just estimate the time to keep things simple. In most cases they do not stop the timers when they take small breaks, which further leads to inaccurate readings. In some cases, people start or stop the time tracking system fraudulently which results in inaccurate billing. Additionally, accurately tracking the time that objects spend interacting is difficult since the objects, absent an interface with a timer, can not start a timer. A person typically needs to be involved in some way. Unfortunately, conventional association systems are not designed to determine and log associations automatically without human intervention.

Conventional object association systems also fail to track multiple tasks, either sequentially or simultaneously. In "time clock" type systems, if there are multiple objects or tasks to be tracked, multiple timers are typically used. These timers can track when a human operator notes that two devices begin to interact, but the problem rapidly becomes too complex to record if there are multiple devices interacting with other devices. Conventional wireless tether systems are limited to noting when two devices are close to each other. They are typically not equipped to handle multiple object interactions where starting and stopping is involved. The location system solutions simply show that multiple devices are in the same space. They do not show which object is interacting with another nor the times of these interactions as they have difficulty in determining interaction detail. Additionally, most current systems do not have the ability to automatically and to continuously track object interactions, such as tracking the progress of a piece of work in process (WIP) and the time it spends interacting with various tools and people, in order to make that information available in "real time" to an interested party. Without this ability to review real-time object association data, supervisors or systems have difficulty in quickly recognizing problems in a production flow.

Sites where location systems are used, such as hospitals, may be large and complex. This can make tracking resources within the site, such as a hospital, a complicated task. As such, it may be useful to subdivide the site into locales of interest. As used herein, the term locale is intended to include any area, site, location or point of interest. For example, hospitals have several types of specialty purpose rooms such as patient rooms, emergency rooms, operating rooms, intensive care rooms, quarantine rooms, laboratories, equipment rooms, etc. Each of these rooms can constitute a locale within the hospital. Indeed, such locales are typically the level of granularity for locations that hospitals typically work with. For example, patients are assigned to rooms, samples are sent to laboratories, and doctors schedule the use of operating rooms. Associating an object or person with such a locale provides a convenient level of granularity for tracking resources as well as providing context for the calculated location of the object or person. For example, knowing a doctor is in an operating room may be more useful than knowing that the doctor is at coordinates X, Y, Z.

In many instances, an interaction between an object and another object may be inconsequential. For example, a doctor may pass within a close proximity of a patient on the way to treat another patient. If criteria for association were based solely on proximity, such passing proximity could be determined to be an association between the doctor and the patient even though the doctor had no actual interaction with the patient. Likewise, the limitations of the hardware used to determine location may cause the location of an object or person to briefly change or to show inconsistent location. For example, a doctor may be in a first locale, such as a room, that is directly adjacent to a second locale, such as another room. If the doctor is against a wall in the first room that is adjacent to the second room, it is possible that the calculated location of the doctor may show that the doctor is suddenly in the second room and then back in the first room even though the doctor never actually changed rooms. In both of these examples, the interaction of the doctor with a patient or locale was too brief for an actual interaction to occur, and therefore an association between the doctor and the patient or locale should be not formed.

SUMMARY OF THE INVENTION

Accordingly, it would be beneficial to be able determine associations between an object or person being tracked and another object or person, location, or locale based on the time of interaction as well as the proximity of the object to another object, location, or locale.

In accordance with one embodiment, a system is provided for associating an object with a locale or a second object. The system includes an object identifier, and location determining module. The object identifier is linked with an object and provides data identifying the object. The location determining module determines the location of the object and includes an object location module and an object association module. The object location module determines the location of the object based at least in part on the data. The object association module associates the object with a second object or locale. The object association module is configured to determine, based on the location of the object, whether the object is in proximity to the second object or the locale for a time period greater than or equal to a threshold time. If the time period that the object is in proximity to the second object or the locale is greater than or equal to the threshold time, the object association module is configured to create an association between the object and the second object or the locale.

In accordance with another embodiment, a method is provided for associating an object with a locale or a second object. The method includes providing, on object identifier linked with an object, data identifying the object. An object location module may then determine the location of the object, based at least in part on the provided data identifying the object. An object association module may then create an association between the object and a second object or locale based on the location of the object and whether the object is in proximity to the second object or the locale for a time period greater than or equal to a threshold time.

DETAILED DESCRIPTION

The illustrative embodiment of the present invention provides a method of tracking, calculating or determining associations using a location system. Locations of objects are determined based on signals transmitted from object identifiers linked to the objects and forwarded to a location determining device. As used herein the term link is intended to mean that the object identifier is associated, coupled, connected or affixed, either directly or indirectly, to the object in any suitable manner. The origin of the signal is calculated based on several factors including, but not limited to, the known position of the receivers receiving the signal, the historical recorded position of the object, the characteristics of the receivers receiving the signal (i.e. the range), the strength of the received signal, the type of signal, and whether or not the signal was repeated. Those of ordinary skill will be able to determine other methods of determining location that are consistent with the teachings of the present invention. The location is determined by a location determining module. Once the location of the object has been determined, the location determining module can determine associations between the located object and other objects or locales based on the amount of time the located object is in proximity to the other object or locale. Once an association is determined, it may be processed or stored as well as the duration of the association. The identified associations may then be leveraged in a number of ways by other applications interfaced with the network, such as by being used in billing systems, inventory systems, asset management systems, and automatic event generation systems based on the identified association.

As used herein, the term object is intended to include any portable or non-portable item or thing of any size, shape or dimension, a person, an entity, or a mammal or non-mammal, that can be used or associated with the object identifier of the present invention.

As used herein, the term network is intended to include a Local Area Network (LAN), a Wide Area Network (WAN), a metropolitan network, an intranet, the Internet, a satellite network, or some other type of network. Communication may be established with the network through a variety of connections including, but not limited to, standard telephone lines, LAN or WAN links (e.g., 802.11, T1, T3, 56 kb, X.25), broadband connections (e.g., ISDN, Frame Relay, ATM), wireless connections such as Bluetooth cellular, or GSM, or some combination of any or all of the above. In order to interface with the network, a network interface may be provided. The network interface may be a FireWire interface, FlexRay interface, RS-232 interface and may include a built-in network adapter, network interface card, PCMCIA network card, card bus network adapter, wireless network adapter, USB network adapter, modem or any other suitable device.

Figure 1:
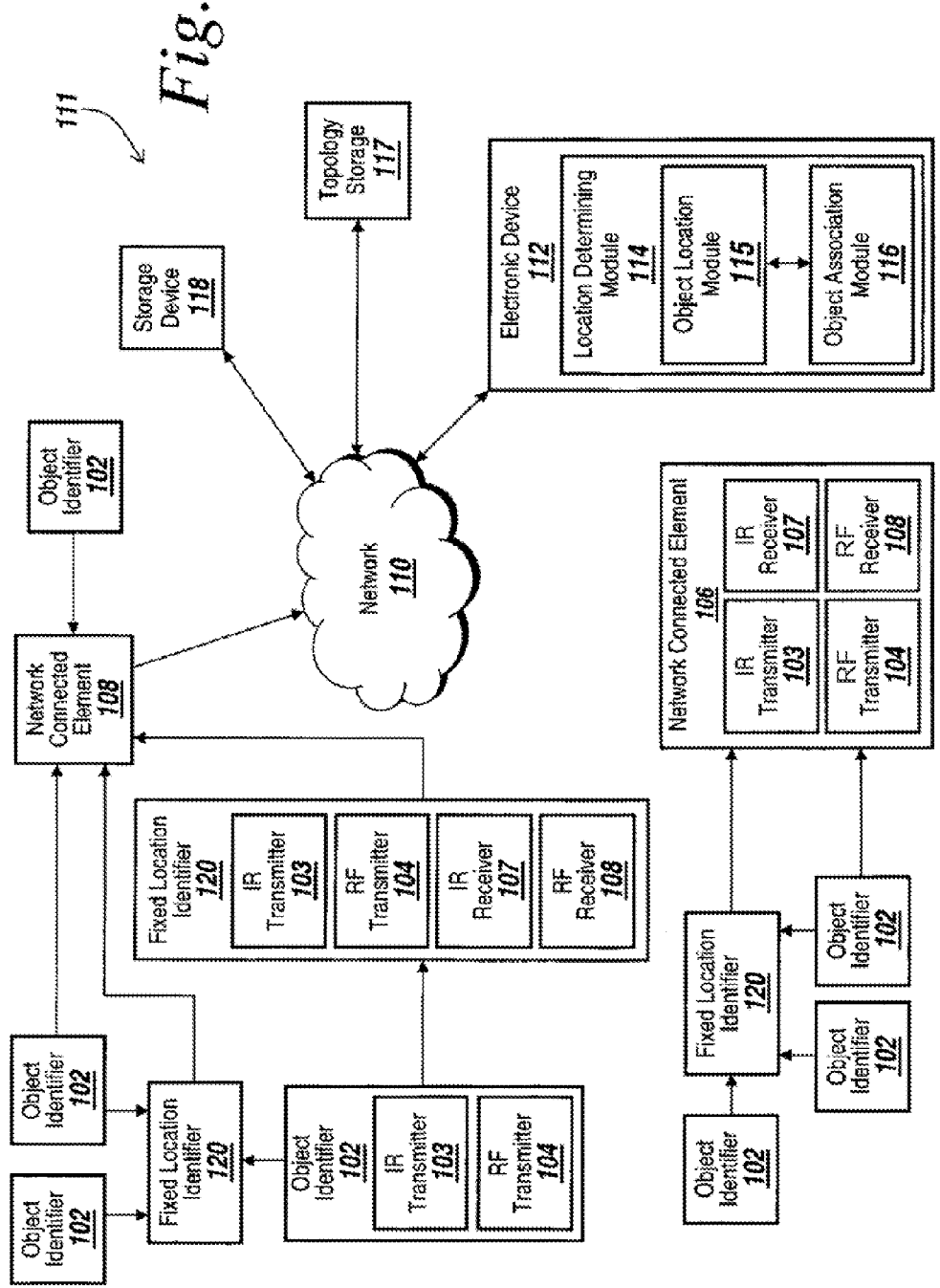
FIG. 1 depicts a block diagram of an environment suitable for practicing an illustrative embodiment.

FIG. 1 depicts one embodiment of a location system 111 suitable for practicing an illustrative embodiment of the present invention. A plurality of object identifiers 102 linked to objects include one or more transmitters which are used to generate a signal which is sent to a network connected element 106. The one or more transmitters may include a radio frequency (RF) transmitter, an infrared (IR) transmitter, an ultrasonic (US) transmitter, transceivers, or any combination thereof. In the example of FIG. 1, the object identifiers 102 include one or more of an IR transmitter 103 and a RF transmitter 104. The transmitted signal may include a unique identifier identifying the object identifier and by extension the object to which it is linked. The network connected element 106 may include one or more transmitting components as well as one or more receiving components. The one or more transmitting components may include one or more of a radio frequency (RF) transmitter, an infrared (IR) transmitter, an ultrasonic (US) transmitter, transceivers, or any combination thereof. The one or more receiving components may include one or more of a radio frequency (RF) receiver, an infrared (IR) receiver, an ultrasonic (US) receiver, a transceiver, or any combination thereof. In the example of FIG. 1, the network connected element 106 includes one or more of an IR transmitter 103, an RF transmitter 104, an IR receiver 107 and an RF receiver 108. The IR receiver 107 is capable of receiving an IR signal generated by the object identifier 102. The RF receiver 108 is capable of receiving an RF signal generated by the object identifier 102.

The network connected element 106 is interfaced through a network interface with a network 110 and forwards the signal received from the object identifier 102 to an electronic device 112 which is also interfaced with the network 110. The interface between the network connected element 106 and the network 110 may be a physical interface in the case of a wired network, or a wireless interface in the case of a wireless network. Although the object identifier 102 and network connected element 106 have been described as including IR and RF transmitters 103 and 104 and receivers 107 and 108, those skilled in the art will recognized that other configurations and receiver and transmitter combinations are possible, without departing from the scope of the present invention.

The electronic device 112 may include any electronic or computer system such as a workstation, desktop computer, server, web server, or laptop, a handheld device, sensor, actuator or other form of computing or telecommunications device that is capable of wireless or wired communication with the network and that has sufficient processor power and memory capacity to perform the operations described herein. The electronic device 112 includes a location determining module 114 which is used to locate the object identifier 102 and the corresponding object to which the object identifier is linked.

The location determining module 114, according to one embodiment of the present invention, includes any appropriate software and hardware for determining or deriving location information about an object, for tracking time that objects and/or locales interact with each other, and for forming associations between objects and/or locales.

The location determining module 114 illustrated herein includes an object location module 115 and an object association module 116. The object location module 115 is configured to determine the location of the object identifier and hence the object linked thereto based at least in part on data identifying the object provided by the object identifier 102.

The object location module 115 of the location determining module 114 calculates the origin of the signal using one or more factors including, but not limited to, the known position of the receivers receiving the signal, which is retrieved from topology storage device 117 which is also interfaced with the network 110, the historical recorded position of the object, the characteristics of the receivers receiving the signal (i.e. the range) which are retrieved from storage device 118 also interfaced with the network, the strength of the received signal, the type of signal, and whether or not the signal was repeated (which are determined by analyzing information contained in the signal received from the network connected element 106). This list of factors is not intended to be exhaustive and can include other known factors or methodologies as set forth below. Examples of suitable systems and/or methodologies for determining location that can be employed by the object location module 115 are described in U.S. Patent Publication No. 20020198986 and U.S. Pat. Nos. 7,053,831; 7,099,895, assigned to the assignee hereof, and the contents of which are incorporated herein by reference. Other suitable location determining systems and/or methodologies that can be employed in the present invention include active and passive RFID systems, barcode systems, magnetic cards, fixed beacon type systems, triangulation systems, time-of arrival and derivative time of arrival systems, and dead reckoning systems.

The illustrated location determining module 114 also includes an object association module 116, which according to one embodiment of the present invention communicates with the object location module 115. The object association module 116 is configured to determine based on the location of the object received from the object location module 115 whether the object is in proximity to another object or a locale for a time period greater than or equal to a threshold time. If the time period that the object is in proximity to the second object or the locale is greater than or equal to the threshold time, the object association module 316 is configured to create an association between the object and the second object or the locale.

Although the location determining module 114 will usually be implemented as a software component, the location determining module 114 may also be implemented by being hardwired into a device.

The object identifier may be directly or indirectly linked by any suitable fastening or joining mechanism to the object. For example, the object identifier 102 may be directly linked to a person who is wearing it as a medical bracelet. Alternatively, the object identifier 102 may be indirectly linked such as by being embedded in a name tag which is fastened to clothing. As long as the object identifier 102 travels with its linked object it can identify the location of the object. The location determining module 114 uses the unique identifier to calculate the current location of the object identifier. Once a calculation or determination of the location of the object identifier 102 has been made, the location of the object may be analyzed to see if it reveals object associations or more specifically, can be associated with other objects or locales. The process of analyzing the calculated location of the object identifiers is described in more detail below. Any identified associations may be stored in the storage device 118.

The topology storage device 117 also interfaces with the network 110. The topology storage device 117 stores the topology data used by the location determining module 114 to determine the location of the object identifier 102. The topology data may store topology data of any suitable type, such as floor plans for the site or locale the location system 111 is deployed in and/or the locations of the network connected element 106 and/or the fixed location identifier 120 that may be deployed at the site. Using this information, the location determining module 114 is able to determine the location of the object identifier 102 (as well as network connected element 106 and fixed location identifier 120) in relation to known structural features of the site (e.g. floors, wards, hallways, rooms, and the like).

In one aspect of the illustrative embodiment of the present invention, a fixed location identifier 120 is also present in the location system. The fixed location identifier 120 may include one or more transmitters as well as one or more receivers. The transmitters may include one or more RF, IR, US transmitters, transceivers, or any combination thereof. The receiver can include one or more RF, IR, or US receivers, or any combination thereof. As illustrated in FIG. 1, the fixed location identifier 120 can include an IR transmitter 103, an RF transmitter 104, an IR receiver 107 and an RF receiver 109. The IR receiver 107 is capable of receiving an IR signal generated by the object identifier 102, while the RF receiver 108 is capable of receiving an RF signal generated by the object identifier 102. The location of the fixed location identifier 120 is stored in the topology storage device 117. After receiving a signal from the object identifier 102, the fixed location identifier appends its own identifier (unique or nonunique) to the signal and transmits the signal to the network connected element 106. When the signal eventually reaches the location determining module 114, the location determining module may use the characteristics of the fixed location identifier 120 (such as location and range) to help determine the location of the object identifier 102. For example, if the location determining module receives notification from both a fixed location identifier 120 and a network connected element 106 that both received an RF signal, the signal can only have originated from a location that is within the range of both receivers. Those skilled in the art will recognize that many alternate implementations are possible within the scope of the present invention.

Figure 2:
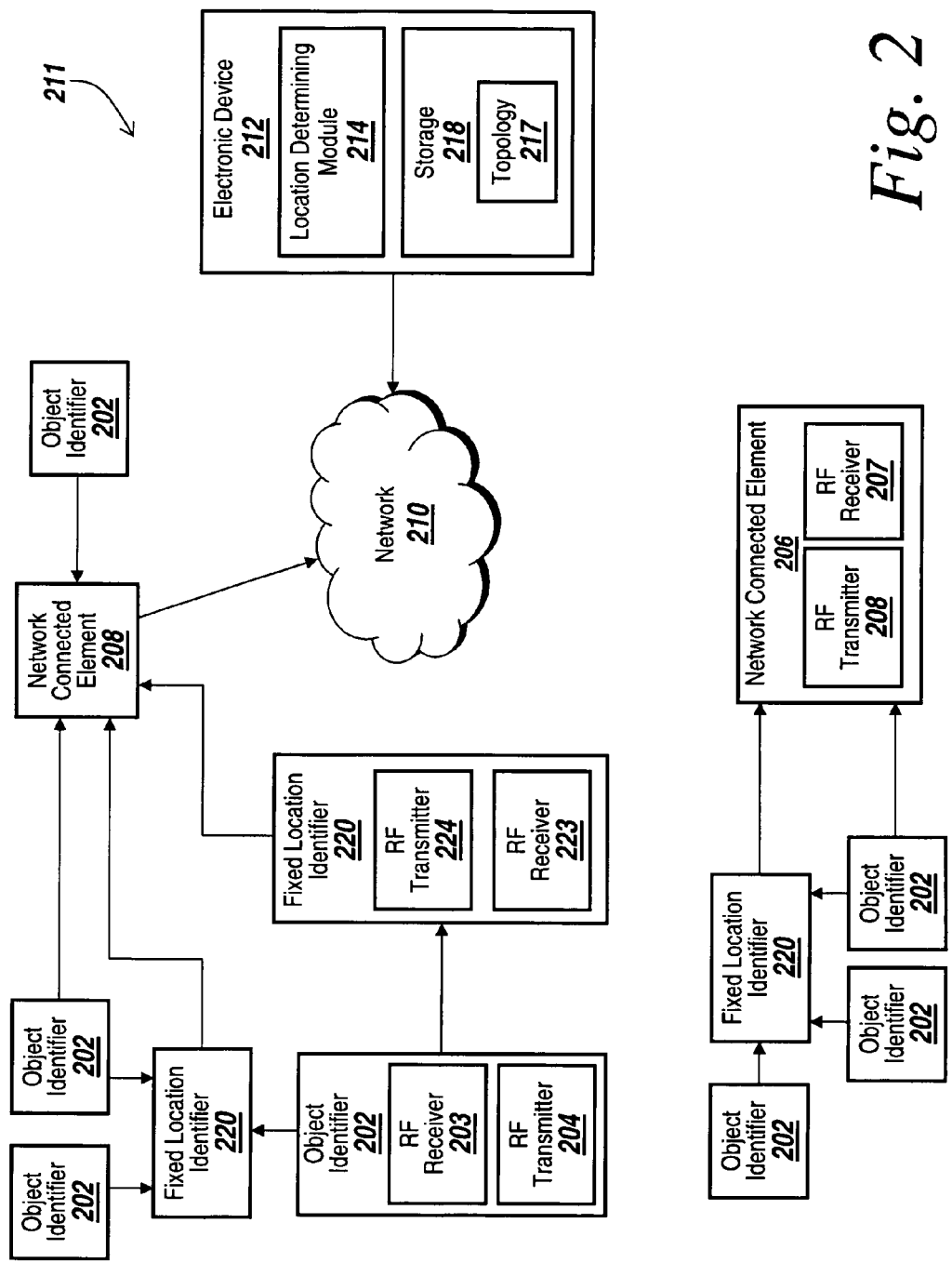
FIG. 2 depicts a block diagram of an environment suitable for practicing an alternate illustrative embodiment.

FIG. 2 is an alternate embodiment wherein the system 211 is implemented using a radio frequency identification (RFID) configuration. Similar to FIG. 1, the system 211 includes a plurality of object identifiers 202 linked to objects, one or more network connected elements 206, a network 210, an electronic device 212 that includes the topology storage device 216 and the location determining module 114, and one or more fixed location identifiers 220. In this embodiment, the object identifiers are configured as passive RFID tags which include an RF receiver 203 and a RF transmitter 204, although the identifiers can also be configured as active RFID tags. Likewise, the network connected elements 206 and fixed location identifiers 220 also include RF receivers 207, 223 and RF transmitters 208, 224.

In operation, the one or more object identifiers 202 are queried by a signal sent from the RF transmitter 208, 224 of a network connected element 206 or a fixed location identifier 220 and received by the RF receiver 203 of the object identifier 202. Because the one or more object identifiers 202 are configured as passive RFID tags, the signal received at the object identifier 202 serves to power the object identifier 202, which in turn generates and transmits a response signal including a unique identifier from the RF transmitter 204. The transmitted response signal may then be received by the RF receivers 207, 223 of a network connected element 206 or fixed location identifier 220. The network connected element 206 is interfaced with a network 210 and forwards the signal received from the object identifier 202 to an electronic device 212 which is also interfaced with the network 210.

In the example of FIG. 2, the electronic device 212 includes a location determining module 214 and storage device 218. The electronic device 212 operates in much the same manner as the electronic device 112 of FIG. 1 except that the storage device 218 for the location data is located on the electronic device 212. Suitable storage devices 218 include any device, component or system that can store digital or analog data, and may include, but is not limited to, memory drives such as hard drives and optical drives, Flash drives, optical media (CDS, DVDs, etc.), EPROM, EEPROM, USB drives or storage elements, RAM, ROM, database software and hardware, removable storage and secondary storage devices, or other suitable storage mediums. In this embodiment, the storage device 218 also includes the topology storage device 217 or information associated therewith. The location determining module 214 is used to locate the object identifier 202 and the corresponding object to which the object identifier is linked. The location determining module 214 operates in the same manner as the location determining module 114 of FIG. 1. The location determining module 214 uses the unique identifier to calculate the current location of the object identifier. The location determining module 214 calculates the origin of the signal using a variety of factors including the known position of the receivers receiving the signal, which is retrieved from topology data 216, the historical recorded position of the object, the characteristics of the receivers receiving the signal (i.e. the range) which are retrieved from storage device 218, the strength of the received signal, the type of signal, and whether or not the signal was repeated which is determined by analyzing information contained in the signal received from the network connected element 206. Once a calculation or determination of the location of the object identifier 202 has been made, the location of the object may be analyzed to see if it reveals object associations, or the objects can be associated with one or more other objects. The process of analyzing the calculated location of the object identifiers is described in more detail below. Any identified associations may be stored in the storage device 218.

The network connected elements 206 and fixed location identifier 220 of FIG. 2 operate similar to the network connected elements 106 and fixed location identifier 120 of FIG. 1. Both devices 206, 220 are configured to query the object identifier 202, receive the response signal sent from the object identifier 202 in response to the query signal, and pass the information including the unique identification from the received signal to the location determining module 214. The fixed location identifier 220 and the network connected element 206 may also add information to the information present in the received signal. When the signal eventually reaches the location determining module 214, the location determining module 214 may use the information added by the fixed location identifier 220 and the network connected element 206 to help locate the object identifier 202.

Figure 3:
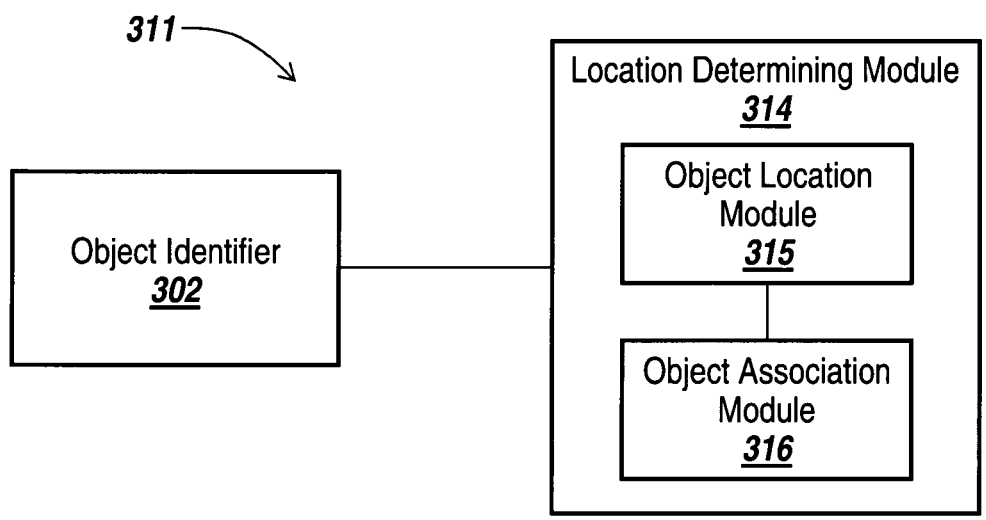
FIG. 3 depicts a block diagram of an alternate environment suitable for practicing an illustrative embodiment of the present invention not utilizing a network.

A non-networked form of the illustrative embodiment of the present invention may also be implemented. FIG. 3 depicts a block diagram of a location system 311, suitable for determining object association without relying on the use of a network. The system 311 includes an object identifier 302 linked with an object and a location determining module 314.

The object identifier 302 provides data which identifies the object to the determining module 314. The object identifier 302 may transmit a signal including the identifying data using a transmitting component to transmit a signal. The transmitting component may be a transmitter, transceiver, transponder or similar device. In other embodiments, the data identifying the object may provided by a passive technology such as RFID, barcoding, or magnetic encoding which require a reader to obtain the identifying data.

The location determining module illustrated herein includes an object location module 315 and an object association module 316, as set forth above. The object location module 315 is configured to determine the location of the object identifier based at least in part on data identifying the object provided by the object identifier 302. The object association module 316 is configured to determine based on the location of the object, as determined by the object location module 315, whether the object is in proximity to a second object or a locale for a time period greater than or equal to a threshold time. If the time period that the object is in proximity to the second object or the locale is greater than or equal to the threshold time, the object association module 316 is configured to create an association between the object and the second object or the locale.

The location determining module 314, including the object location module 315 and object association module 316, may include any structure suitable for determining location, keeping track of time, and forming associations. Examples may include any device capable of determining the location of one or more object identifiers, keeping track of time, and forming associations based on proximity and time. According to various embodiments of the invention, the location determining module 314 may be an electronic device. The electronic device may take multiple forms and may include, a processor, a computer, a personal digital assistant, a communications device, such as a cell phone, a network appliance, a web server, a network, any device capable of manipulating information, a receiver, a transmitter, an interface or any combination of these devices. Further, those of ordinary skill in the art will recognize that the location determining module 314 can be integrated into different parts of the location system 311. For example, the location determining module can form part of a network connected element, a fixed location identifier, an object identifier, or can be separate from and/or remotely located from the other system components.

According to various embodiments of the invention, the location determining module 314 may be capable of performing additional functionality, such as receiving requests for information, providing information, storing information, commanding actions in response to location information, associating objects with other objects or with locations, establishing privacy conditions regarding availability of location information, interfacing directly with various network types, and the like. According to further embodiments of the invention, the location determining module 314 includes multiple, distributed receivers or readers, some of which may be connected to a network, and others not connected to a network. According to various embodiments of the invention, the object identifier 310 and location determining module 314 utilize RF signals for the determination of location.

Those skilled in the art will recognize that different types of components capable of transmitting and receiving signals may be used in place of the illustrated transmitters and receivers depicted herein. For example, a transceiver may be substituted for a receiver without departing from the scope of the present invention.

Figure 4A:
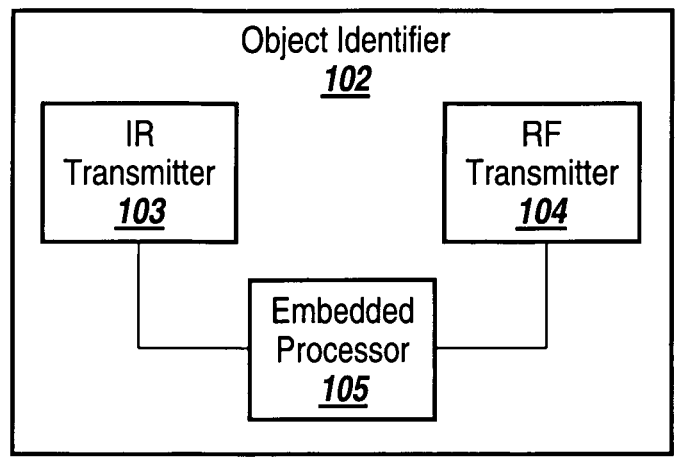
FIG. 4A depicts a block diagram of an object identifier used by the illustrative embodiment of FIG. 1.
Figure 4B:
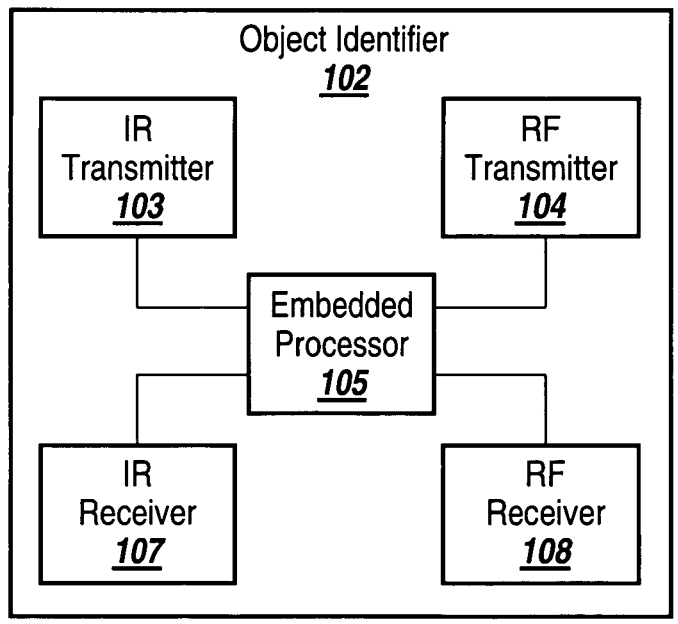
FIG. 4B depicts a block diagram of a fixed location identifier used by the illustrative embodiment of FIG. 1.

FIG. 4A depicts a block diagram of an object identifier 102, similar to the one used, for example, in FIG. 1. As illustrated, the object identifier 102 includes an IR transmitter 103 and an RF transmitter 104. Both transmitters are controlled by an embedded processor 105 which controls the signaling process. Similarly, FIG. 4B depicts a block diagram of a fixed location identifier 120 used for example in FIG. 1. The fixed location identifier 120 includes an IR transmitter 103 and an RF transmitter 104 which are controlled by an embedded processor 105 which controls the signaling process. Also included in the fixed location identifier 120 are an IR receiver 107 and an RF receiver 109 which are used to receive signals from the object identifier 102.

The signaling process may employ both RF and IR signals in alternating combination. According to one embodiment of the invention, the RF signal is transmitted every ten seconds and the IR signal is transmitted every twenty seconds. This method provides a substantially consistent IR power level, while varying an RF power level. Varying the RF power level may assist in determining a location of the object identifier 102 by enabling the network connected element 106 to receive less than all of the RF signals. The transmitted signals may also include additional information such as the signal strength being transmitted, the period between transmissions, the length of time of the transmissions, a unique identifier for the object identifier 102, information received from one or more input devices and/or various status information, such as those pertaining to the components of the object identifier. In one aspect of the invention, the object identifier 102 also contains receivers and the location determining module 114 configures the object identifier over the network 10 by sending transmission parameters (i.e.: alternate signals every 30 seconds). Since IR signals are line-of-sight signals and RF signals travel through walls, the combination of signals may be used by the illustrative embodiment of the present invention to locate signals with greater accuracy than would be possible using either form of signaling alone.

Figure 4C:
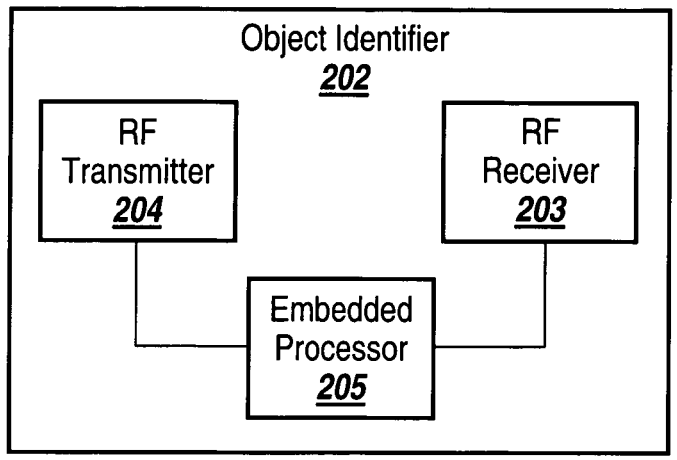
FIG. 4C depicts a block diagram of an object identifier used by the illustrative embodiment of FIG. 2.
Figure 4D:
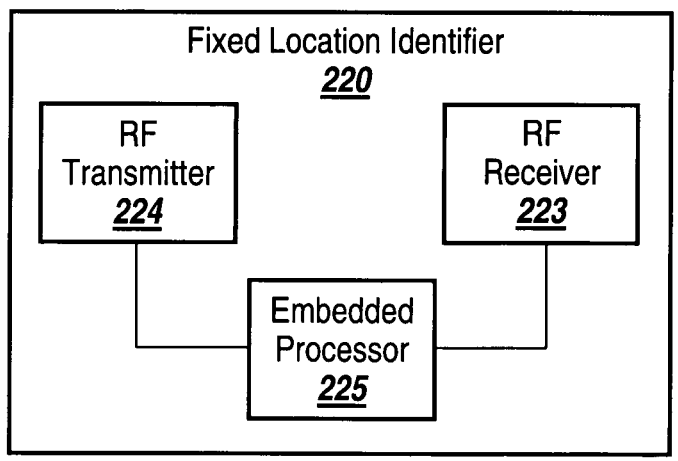
FIG. 4D depicts a block diagram of a fixed location identifier used by the illustrative embodiment of FIG. 2.

FIG. 4C depicts a block diagram of an object identifier 202 used in an alternate embodiment depicted in FIG. 2. Accordingly, The object identifier 202 includes an RF receiver 203 and an RF transmitter 204. Both the receiver 203 and transmitter 204 are controlled by an embedded processor 205 which controls the signaling process. Similarly, FIG. 4D depicts a block diagram of a fixed location identifier 220 used by the alternate embodiment depicted in FIG. 2. The fixed location identifier 220 includes an RF receiver 223 and an RF transmitter 224 which are controlled by an embedded processor 225 which controls the signaling process.

As discussed previously in regard to FIG. 2, the object identifier 202 is configured as a passive RFID tag. As such, the RF transmitter 204 and embedded processor 205 of the object identifier rely on the power provided by an RF signal from the RF transmitter 224 of the fixed location identifier 220. In operation, the embedded processor of the fixed location identifier 220 directs the RF transmitter 224 to send a query signal. The query signal is received by the RF receiver 203 of the object identifier 202 and energizes the embedded processor 205 and RF transmitter 204. The embedded processor 205 interprets the query signal and directs the RF transmitter 203 to transmit a response signal providing a unique identifier. The response signal is received at the RF receiver 223 of the fixed location identifier 220 and processed by the embedded processor. The embedded processor 225 may then append additional information to the information of the response signal and direct the RF transmitter 224 to transmit a signal including the information from the response signal and the additional information.

The advantage of such passive RFID design is that it does not require a power source on the object identifier 202. This also reduces the build cost of the object identifier 202. Those of ordinary skill will recognize that the object identifiers can also be constructed as active RFID tags, if desired.

Figure 5:
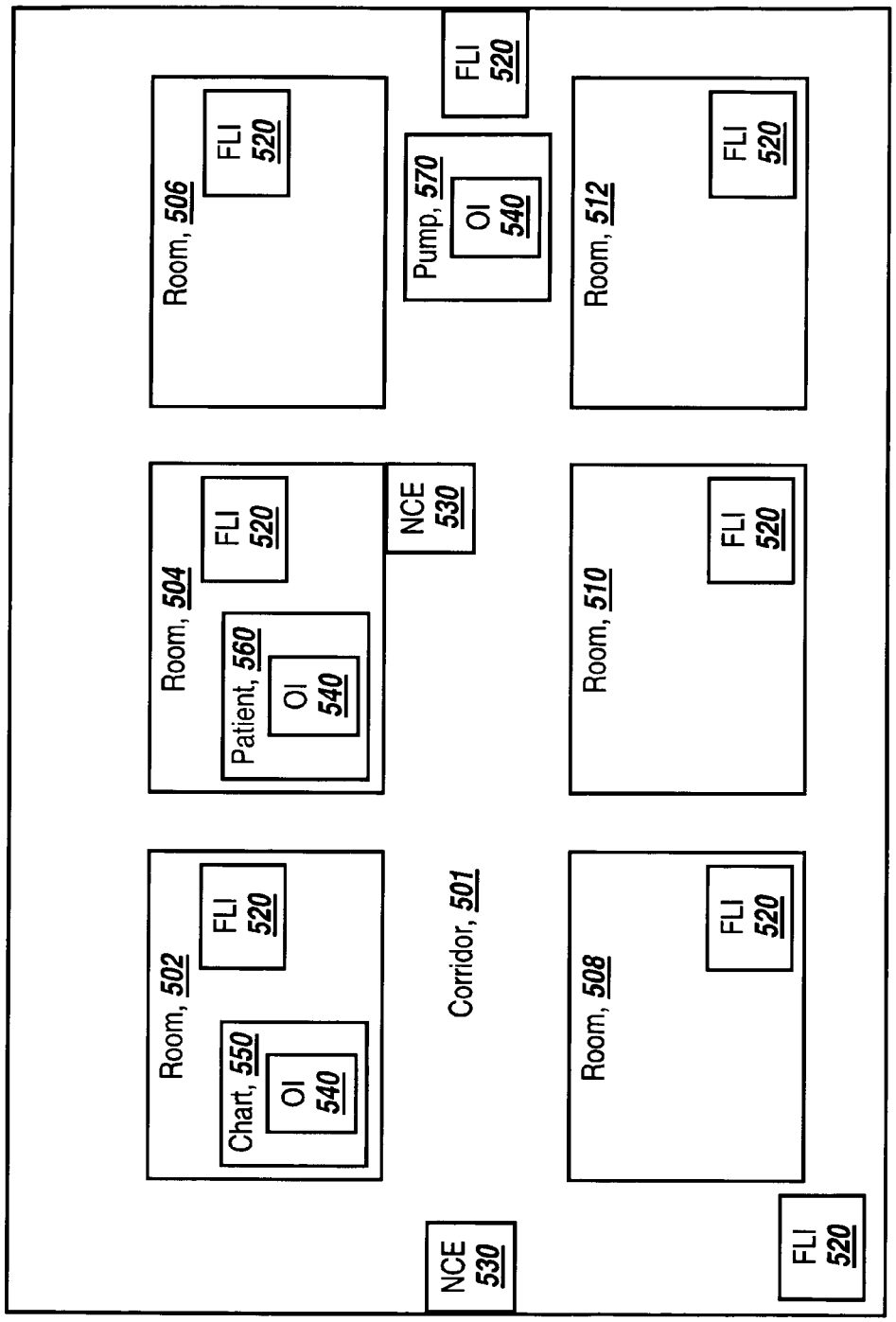
FIG. 5 depicts a block diagram of the layout of a hospital practicing an illustrative embodiment of the present invention.

FIG. 5 depicts a block diagram of a layout of a hospital 500 using the illustrative embodiment of the present invention. The hospital lay-out can be pre-stored in the topology storage device 117. The hospital 500 includes a plurality of rooms 502, 504, 506, 508, 510 and 512 which may also be considered locales. Each of the rooms 502, 504, 506, 508, 510 and 512 has a fixed location identifier (FLI) 520 within the room. A corridor 501 has an additional fixed location identifier 520 at one end of the corridor and a couple of network connected elements (NCE) 530 located in the middle of the corridor and end of the corridor. The fixed location identifiers 520 and network connected elements 530 may be any of the implementations previously discussed, such as those in FIGS. 1 and 2, or any number of other implementations. As previously noted, the network to which the network connected element 530 is connected may be a wired or wireless network with the result that the network connected element 530 may or may not be physically connected to the network. The illustrative embodiment of the present invention is designed to execute over pre-existing networks and does not require the creation of a proprietary network. The hospital includes a plurality of objects to which object identifier's (OI) 540 have been linked. One room 502 includes a patient chart 550 with an object identifier 540 attached to the chart so that it will not be misplaced and may be quickly retrieved. Another room 504 includes a patient 560 who is wearing an object identifier 540 either attached to a piece of clothing or as a bracelet. The object identifier 540 attached to the patient 560 allows the patient's movements to be tracked throughout the hospital. Out in the corridor 501, an object identifier 540 is linked to an infusion pump 570. The object identifier 540 allows quick location of the infusion pump 570 in the event another unit of the hospital borrows the pump in an emergency without time to inform the proper people working in the hospital unit to which the pump is assigned. The object identifiers 540 may be any of the implementations previously discussed, such as those in FIGS. 1 and 2, or any number of other implementations.

The use of the network connected elements 530 and the fixed location identifiers 520 may be illustrated with an example. The object identifier 540 linked to the infusion pump 570 may be configured to emit one or more signals bearing a unique identifier. If the infusion pump 570 is located in a corridor 501, an RF signal transmitted by the object identifier is received by the receivers located in the fixed location identifiers 520 in a number of rooms 504, 506, 510 and 512 as well as the fixed location identifier 520 at the end of the corridor nearest to the pump. Additionally, the signal may also be received by the network connected element 530 located outside room 504. If the object identifier 540 linked to the infusion pump 570 also transmits an IR signal, it is only received by the fixed location identifier 520 located at the end of the corridor 501 and the network connected element 530 located outside room 504, since IR signals are line-of-sight signals. Since line-of-sight signals do not travel through most walls, they are unlikely to be received by an IR receiver located within one of the hospital rooms 502, 504, 506, 508, 510 and 512. The network connected element 530 located outside room 504 and the fixed location identifier 520 located at the end of the corridor 501 report receiving both signals to the location determining module (not shown). The location determining module uses the known location of both the network connected element 530 outside room 504 and the fixed location identifier 520 at the end of the corridor 501 to determine location. If both the network connected element 530 and fixed location identifier 520 are configured to received both types of signals, it can be determined that the infusion pump 570 must be in the corridor 510. Furthermore, since the fixed location identifier 520 may have a smaller receiving range for RF signals than the network connected element 530, it may be determined that the infusion pump 570 is located not only in the corridor but within range of the RF receiver on the fixed location identifier 520. Alternately, signal strength may be used in determining proximity to a receiver. The receiving ranges of the RF receivers and transmission strength of RF transmitters are an implementation choice, and those skilled in the art will recognize that they may be adjusted without departing from the scope of the present invention.

Once the location determining module has determined the current location or locale of an object to which an object identifier 540 is linked, the location is compared against the current location of other objects or locales to determine the proximity of the located object to the other objects or locales. The pre-determined location is usually a place of special interest such as a bed. The locale, in for example a hospital environment, may be a room. If the object is within a pre-defined distance of another object or locale the location determining module determines that the two objects or the object and the locale are interacting, and records an association in the storage device. Those of ordinary skill will readily recognize that the proximity or distance relationship of one object or locale with another object or locale can be varied based upon user requirements or needs. The appropriate proximity or distance can be pre-selected or predetermined, or can be derived, calculated or determined in real time. Those of ordinary skill will be readily able to determine the appropriate proximity based upon one or more factors, including but not limited to the type of object, the status of the object, locale, previous interactions or associations, the environment in which the system is used, and/or user requirements or specifications.

The location determining module may require the association to occur for a minimum or threshold period of time before deciding an association is occurring. This helps prevent false associations. The threshold period of time can be pre-selected or predetermined, and hence stored, in the system 111. Threshold times may be calculated, derived or otherwise established based on one or more factors including, but not limited to, user input, system specifications, the type of object, the status of the object, the locale, previous interactions or associations, the environment in which the system is used, user requirements or specifications, or the like. Moreover, the threshold time can also be calculated or determined in real time based upon one or more of the above listed parameters. Those of ordinary skill will also recognize that the threshold time value used to determine associations can vary as a function of one or more of the foregoing parameters. For example, the personnel, such as doctors, nurses, or janitorial staff may be able to interact with different objects and/or locales in different manners that take different amounts of time. For example, a nurse may be able to interact with a patient much quicker than a doctor. Therefore, the threshold time for associating a nurse with a patient may be smaller than a doctor's with the same patient.

Further, as set forth above, a doctor may pass within a close proximity of a patient on the way to treat another patient. If criteria for association were based solely on proximity, such passing proximity could be determined to be an association between the doctor and the patient even though the doctor had no actual interaction with the patient. Thus, a threshold value may be set as a minimum or threshold time limit that an object being tracked needs to be in proximity to another objector locale before an association is established. If the threshold value is not met, then an association is not established.

In another example, a doctor may be in a first locale, such as a room, that is directly adjacent to a second locale, such as another room. If the doctor is against a wall in the first room that is adjacent to the second room, it is possible that the calculated location of the doctor may show that the doctor is suddenly in the second room and then back in the first room even though the doctor never actually changed rooms. If the time the doctor is shown in the second room is less then that it would actually take for the doctor to physically move to the other room, it can be assumed that this change in locale is not an actual change.

For example, a graphical depiction of the doctor's position may look something like:

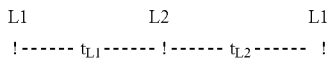

where "L1" is a first locale that corresponds for example to a first room, and "L2" is a second locale that corresponds for example to a second room. The term "$t_{L1}$" corresponds to the amount of time the doctor spends in the first room and the term "$t_{L2}$" corresponds to the amount of time the doctor spends in the second room. Here, the doctor is shown moving from the first room to the second room and back to the first room.

If the time "$t_{L1}$" is greater than or equal to the threshold time and "$t_{L2}$" is less than the threshold time then only an association with the first room is established. As discussed above, the threshold time may depend on the type of object being tracked and the locale it is being associated with. For example, nurses may move between rooms much more quickly than doctors, therefore the threshold times associated therewith may be smaller. The second room "L2" may also be located remotely from the first room "L1", necessitating significant travel time wherein the threshold time would be greater. For example, if the time "$t_{L2}$" is smaller than the time it takes to travel from the first room "L1" to the second room "L2" and back to the first room "L1". It can be assumed that the indication that the doctor was in the second room "L2" to be a false determination by the system.

The association is tracked for a beginning time, ending time, duration, and alternately for separate occurrences, all of which may be stored in the storage device. The electronic device stores, or is interfaced with, a variety of software programs to make use of the object associations determined by the location determining module.

Figure 6:
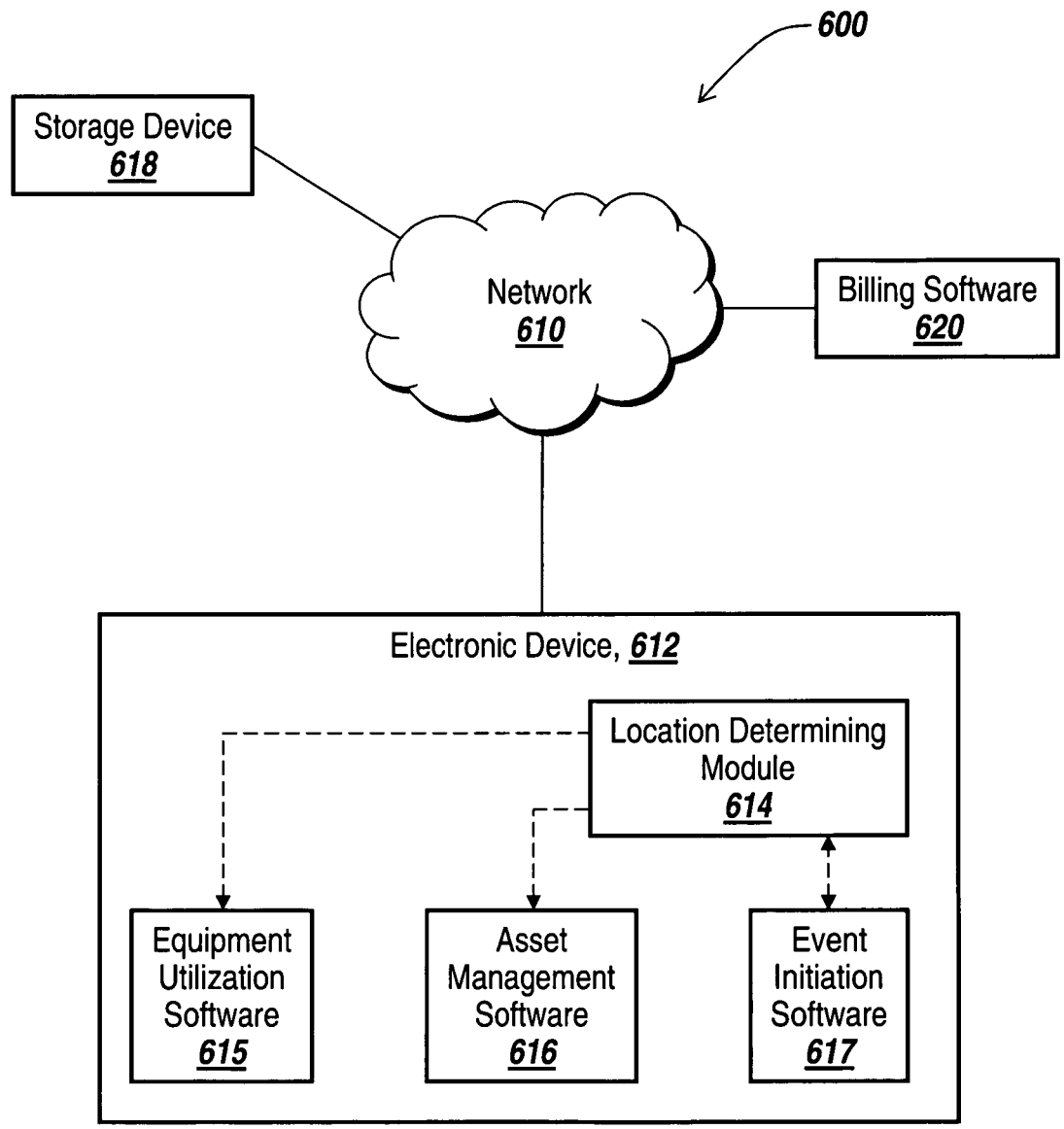
FIG. 6 depicts a block diagram of components of the illustrative embodiment of the present invention used to analyze the associations determined by the location determining module.

FIG. 6 depicts a block diagram 600 of components of an embodiment used to analyze the associations determined by the location determining module 614. The electronic device is similar in many respects to the electronic device illustrated in FIGS. 1 and 2. The location determining module 614 determines object associations and stores records of those associations in the storage device 618. A variety of software components or modules accessible to the location determining module 614 may be used to analyze the object associations. Equipment utilization software 615, asset management software 616 and event initiation software 617 are stored on the electronic device 612. Billing software 620 is interfaced with the network 610. Examples of the different types of software used to analyze object associations determined by the location determining module 614 are explored in more detail below. The software may utilize a JDBC interface located in the location determining module 614 which allows Java applications to send SQL commands to a database on the storage device 618. Those skilled in the art will recognize that the location and types of the various software components utilizing the object associations as input data may change without departing from the scope of the present invention. Those of ordinary skill will also recognize that the determination and/or storage of the object associations can occur at other locations in the illustrated system.

Figure 7:
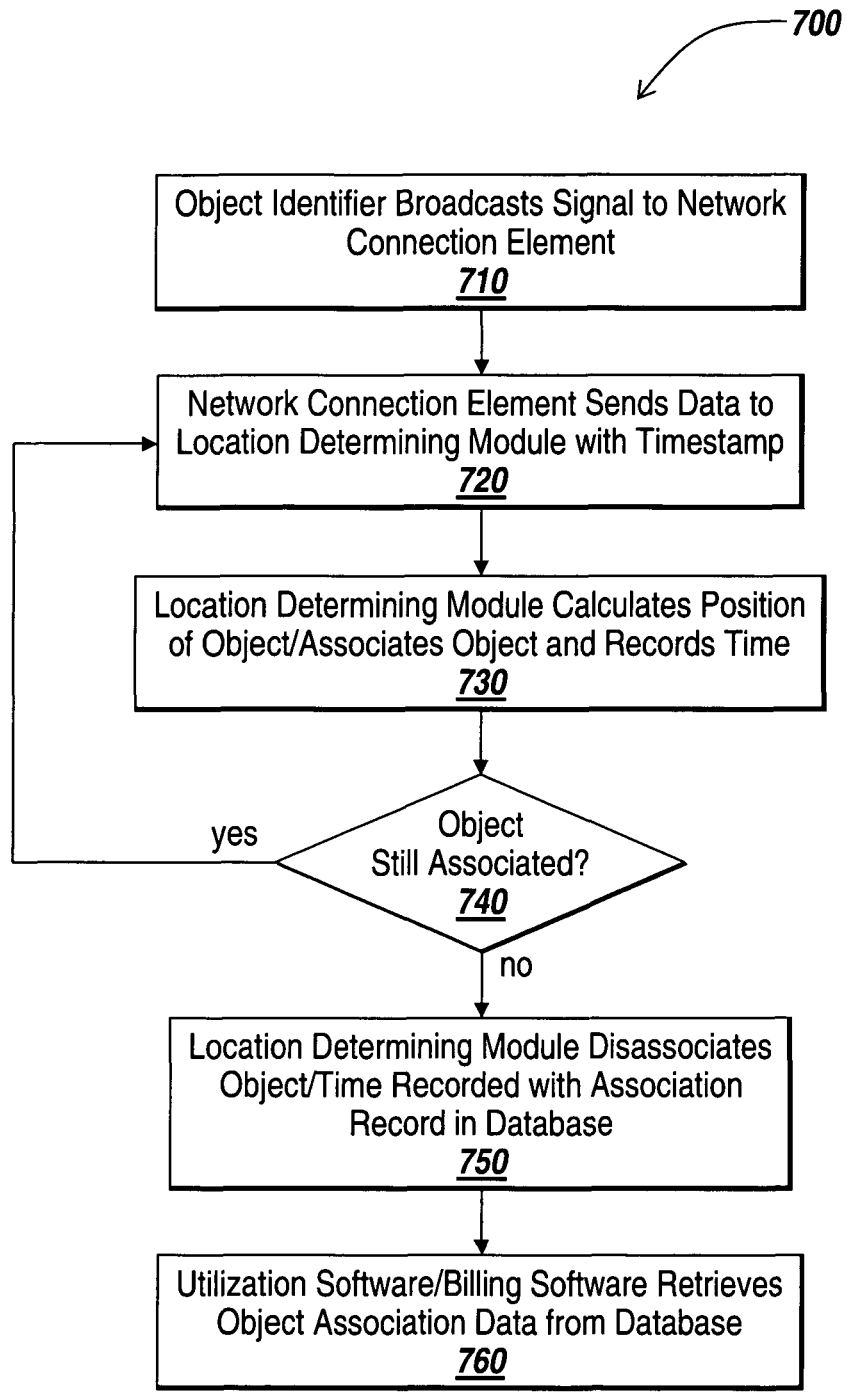
FIG. 7 is a flowchart of the sequence of steps followed by the illustrative embodiment of the present invention to perform equipment utilization analysis and bill generation as a result of object association determined by the illustrative embodiment of the present invention.

Once the object associations have been determined by the location determining module 614, the association data may be provided as input data to a variety of software programs. FIG. 7 is a flowchart 700 of the sequence of steps performed by the illustrative embodiment of the present invention to determine object associations and utilize them in equipment utilization and billing software modules 615 and 620. An object identifier 102, 202, 302, 540 linked to an object broadcasts a signal to the network connected element 106, 206, 530 (step 710). In certain embodiments, such as shown in FIG. 2, the object identifier 202 may transmit the signal in response to a signal sent from the network connected element 206 or a fixed location identifier 120, 220, 520. The signal may be forwarded from a fixed location identifier 120, 220, 520 to the network connected element 106, 206, 530. The network connected element 106, 206, 530 appends information, such as a time stamp and its identifier, onto the signal and sends it to the electronic device 112, 212, and location determining module 114, 214, 314 (step 720). The location determining module 114, 214, 314 calculates the location of the object as outlined above, associates the located object with another object and/or a locale and records the association and the time the association began in the storage device 118, 218, 618 (step 730). The network connected element 106, 206, 530 sends signals received from the object identifier 102, 202, 302, 540 and/or from the fixed location identifier 120, 220, 520 until the association is finished (step 740). Once the network connected element 106, 206, 530 stops sending signals, the location determining module 114, 214, 314, 614 disassociates the object in the storage device 118, 218, 618 and records the time the association ended (step 750). The storage device 118, 218, 618 stores the records of the association which may then be retrieved by the equipment utilization software or billing software 615 and 620 (step 760). The equipment utilization software 615 may use the data to analyze how often a portable x-ray machine is being used in a particular department of a hospital. Alternatively, the object association data may indicate how often a room is being utilized. Similarly, the billing software 620 may use the object association data to determine how much time a surgeon spent in an operating room with a patient in order to determine the amount to bill the patient.

The illustrative embodiment of the present invention may leverage the object association data in a number of ways. In one embodiment, the determined object associations are used to track the movements of a contagious patient in a health care facility. By mapping the calculated locations indicating the individual's path of travel, the health care facility is able to create a response based on which patients were probably exposed to the contagion. In another embodiment, the object identifiers may be linked to prescription drugs. For example, when a bag of intravenous drugs linked to an object identifier forms an association with a patient, a storage device may be consulted to prevent adverse reactions based on other drugs already received by the patient and/or the patient's personal medical history indicating allergies. In another embodiment, the object associations may be used to ensure compliance with HIPPA, the Health Insurance Privacy and Portability Act, which requires that access to a patient's records be limited. By linking object identifiers 102, 202, 302, 540 to staff and the patient's chart, a record may be created indicating who viewed the chart.

Figure 8:
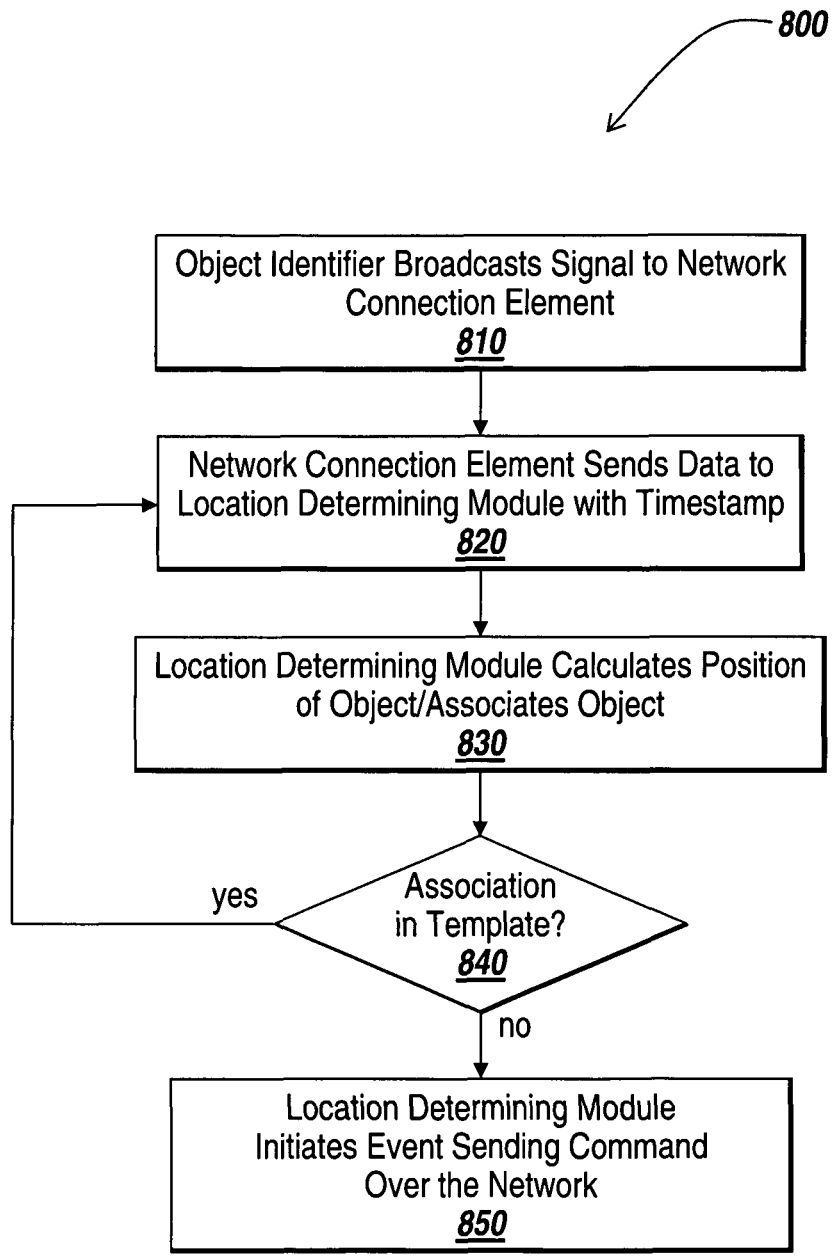
FIG. 8 is a flowchart of the sequence of steps followed by the illustrative embodiment of the present invention to perform event initiation as a result of object association determined by the illustrative embodiment of the present invention.

The object association data stored in the storage device 18 may also be used for event initiation. FIG. 8 is a flowchart 800 of the sequence of steps performed by the illustrative embodiment of the present invention to determine object associations and utilize them in an event initiation software module 617, FIG. 6. The sequence begins when an object identifier 102, 202, 302, 540 linked to an object broadcasts a signal to the network connected element 106, 206, 530 (step 810). In certain embodiments, such as shown in FIG. 2, the object identifier 202 may transmit the signal in response to a signal sent from the network connected element 206 or a fixed location identifier 120, 220, 520. The signal may be forwarded from a fixed location identifier 20 to the network connected element 106, 206, 530. The network connected element 106, 206, 530 appends a time stamp and its identifier onto the signal and sends it to the electronic device 112, 212 and location determining module 114, 214, 314, 614 (step 820). The location determining module 114, 214, 314, 614 calculates the position of the object as outlined above, associates the located object with another object or a locale, and records the association in the storage device (step 830). The association may then be programmatically compared against a template of associations by the event initiation software 617 (step 840). For example, the event initiation software 617 may indicate that if a hospital patient object identifier associates with a corridor, an alarm should be sounded at the nursing station in the applicable hospital unit. Alternately, the event initiation software may indicate that if the object identifier embedded in the name badge of a company CEO becomes associated with an entryway a greeting may be broadcast. If the association is listed in the template, instructions for the event are broadcast on the network 110, 210, 610 (step 850). Those skilled in the art will recognize that other forms of analyzing an object association besides a template may be used without departing from the scope of the present invention.

In one embodiment of the present invention, the object association data is utilized by the asset management software module 616. The asset management software module 616 may be used to provide a real-time inventory of assets owned by a company. The ability to quickly locate items may be of paramount importance in industries such as the health care industry, where a failure to locate an item quickly can result in catastrophic consequences. Additionally, the constant updating of asset locations may result in much lower costs during end of the year inventories. The frequency with which assets transmit their positions is configurable and may be based on how frequently the item is likely to move. For example, for larger machines that move infrequently, the transmitters may be set to signal once an hour or once a day. For smaller items, or items that are frequently being moved, the transmitters may be set to signal once a minute or once every 10 seconds in the case of an object identifier linked to a person. The real-time position of assets may then be broadcast on the network 110, 210, 610 and made available to authorized individuals. In another embodiment, an association may be formed between a bedridden patient and a bed. If it is determined that the association has stopped, an alert is sent over the network to a nurses station to indicate the possibility that the patient has fallen out of bed.

Figure 9:
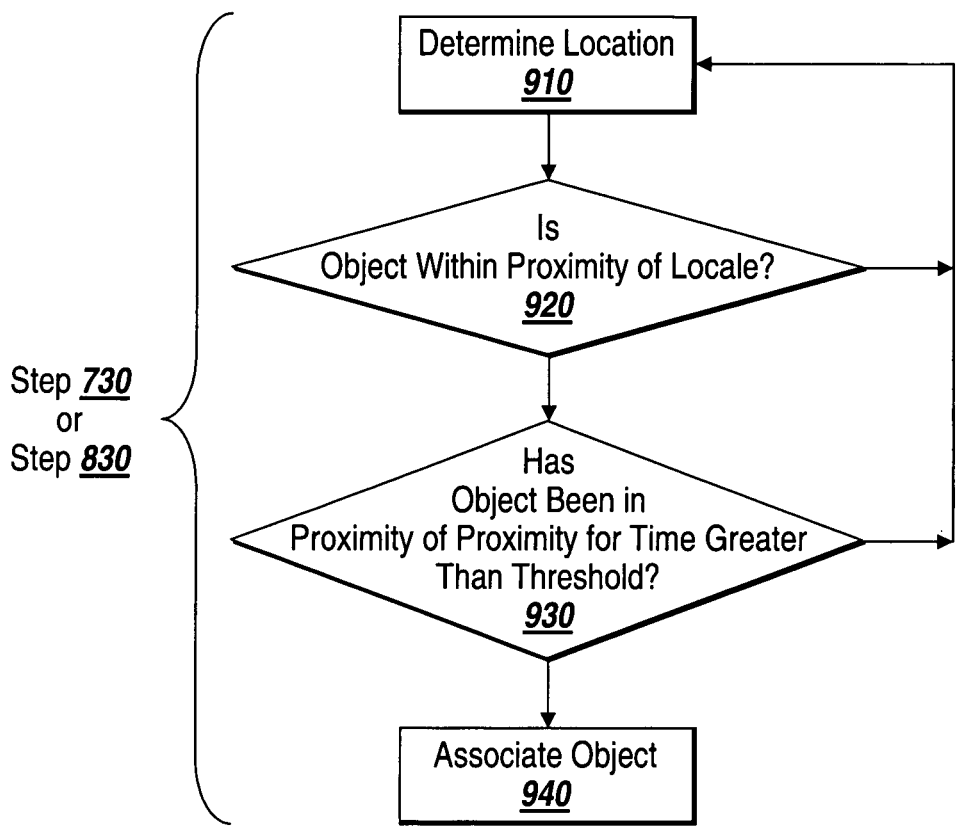
FIG. 9 is a flowchart of the sequence of steps followed by the illustrative embodiment of the present invention to perform object association.

FIG. 9 is a flowchart of the process performed in steps 730 and 830 of FIGS. 7 and 8 by the location determining module 114, 214, 314, 614 of the location system of the present invention. The process begins with the determination of the location for the object to which the object identifier 102, 202, 302, 540 is linked (step 910). In certain embodiments, the determination of location (step 910) may be performed by an object location module 315 of the location determining module 314 as described in relation to FIGS. 1 and 3. Once the location of the object has been determined (step 910), the location information can be used to determine if the object is in proximity to another object or a locale (step 920). If the object is not in proximity to another object or locale, the location of the object is further monitored (step 910). However, if the object is in proximity to another object or a locale, then the time the object is in proximity with the other object or locale may be tracked (step 930). If the time the object is in proximity with another object or locale is less than a threshold time, then the location of the object is further monitored (step 910). However, if the time the object is in proximity with another object or locale is equal to or greater than a threshold time value, then an association for the object can be formed (step 940). The object association may then be used as discussed in relation to FIGS. 6-8.

Although many of the examples listed herein have been made with reference to a hospital environment, the illustrative embodiment of the present invention may be used to detect object associations in a variety of other environments. For example, the object association may take place in the setting of an airport where bags are associated with machinery designated to divert the bags to specific destinations. Alternatively, the object association may be used to verify that each checked bag is associated with a seated passenger before a plane takes off from an airport. The object association may be used to track the movements of products in a store or utilized at a check out register. The object association may be used to identify the effectiveness, or lack thereof, of advertising displays. Since the object association system is designed to work with components which utilize existing network topology, object associations may be determined in many different environments and the environments listed herein are intended merely as illustrative examples and not as an exhaustive list.

It will thus be seen that the invention attains the objectives stated in the previous description. Since certain changes may be made without departing from the scope of the present invention, it is intended that all matter contained in the above description or shown in the accompanying drawings be interpreted as illustrative and not in a literal sense. Practitioners of the art will realize that the sequence of steps depicted in the figures may be altered without departing from the scope of the present invention and that the illustrations contained herein are singular examples of a multitude of possible depictions of the present invention.

I claim:

1. A system for automatically associating an object with a locale or a second object, comprising:
   an object identifier device linked with an object configured to provide data identifying the object,
   a location determining module configured to determine a location of the object, the location determining module including
   an object location module configured to determine the location of the object based at least in part on the data, and
   an object association module configured to associate the object with both of at least one of a second object and a locale, wherein the object association module is configured to determine based on the location of the object whether the object is in proximity to the second object or the locale for a time period greater than or equal to a threshold time, and if the time period that the object is in proximity to the second object or the locale is greater than or equal to the threshold time, the object association module is configured to create an association between the object and the second object or the locale;
   an association template identifying associations among objects and locales whereby observed associations are matched with associations in the association template;
   a network, wherein the location determining module is coupled to the network, and
   a network connected element including at least one signaling component capable of transmitting or receiving signals, wherein the network connected element is configured to receive the data identifying the object provided by the object identifier device and transmit a signal containing the data to the location determining module;
   the object association module further configured to prevent false associations comprising a first locale, a second locale, a time spent in the first locale, and a time spent in the second locale, wherein if the time spent in the first locale is greater than or equal to a false association threshold time and the time spent in the second locale is less than the false association threshold time, association with the second locale is prevented and only an association with the first locale is made, whereby a false association determination is prevented;

the location determining module further configured to disassociate the association between the object and the second object and the object and the locale upon termination of a signal from the object identifier device for the location determined by the object location module;

whereby the association determination and the disassociation are established without input device triggering.

2. The system of claim 1, wherein the object identifier device comprises one or more of
   a transmitter configured to transmit a signal including the data identifying the object,
   a receiver configured to receive a signal requesting the data identifying the object; and
   a processor configured to control the transmitter and the receiver of the object identifier.

3. The system of claim 1, wherein the data identifying the object comprises a unique identifier.

4. The system of claim 1, wherein the data identifying the object is provided in a bar code on the object identifier device or is magnetically encoded on the object identifier.

5. The system of claim 1, wherein the location determining module is part of an electronic device.

6. The system of claim 1, wherein the location determining module further comprises one or more of
   a receiver configured to receive a signal from the object identifier device providing the data identifying the object, and
   a transmitter configured to transmit a request for data identifying the object.

7. The system of claim 1, wherein the object identifier device is a passive RFID device, and the network connected element is a passive RFID reader.

8. The system of claim 1, wherein the object identifier is a bar code, and the network connected element is a bar code reader.

9. The system of claim 1, wherein the location determining module is directly coupled to the object identifier device.

10. The system of claim 1, further comprising a storage device configured to store object associations.

11. The system of claim 1, further comprising a topology storage device configured to store topology data.

12. The system of claim 1, further comprising a fixed location identifier separate and distinct from said object identifier device and having a known location.

13. The system of claim 12, wherein the fixed location identifier comprises at least one receiving component configured to receive transmissions from said object identifier device, and at least one transmitting component configured to transmit a signal.

14. The system of claim 13, further comprising
   a network, wherein the location determining module is coupled to the network, and
   a network connected element including at least one signaling component capable of transmitting or receiving signals, wherein the network connected element is configured to receive the data identifying the object provided by the object identifier device and transmit a signal containing the data to the location determining module, wherein said fixed location identifier transmits said signal to the network connected element, said network connected element incorporating the signal from the fixed location identifier into a signal sent to said location determining module,
   wherein said location determining module uses the known location of said fixed location identifier in the calculation of a location of said object identifier.

15. The system of claim 1, wherein object identifier device is located in a health care facility.

16. The system of claim 15, wherein the locale comprises a room in the health care facility.

17. The system of claim 1, wherein the time period for determining an association depends on the type of object that the object identifier device is linked to.

18. The system of claim 1, wherein the time period for determining an association depends on the location or locale of the object identifier device.

19. The system of claim 1, wherein the time period for determining an association depends on the second object or locale the object identifier device is being associated with.

20. A method for automatically associating an object with a locale or a second object, comprising:
   physically linking, with an object identifier device, the object or the locale;
   providing, on the object identifier device linked with the object or locale, data identifying the object,
   determining, at an object location module computing device, a location of the object based at least in part on the data identifying the object,
   creating, at an object association module computing device, an association between the object and a second object or locale based on the location of the object and whether the object is in proximity to the second object or the locale for a time period greater than or equal to a threshold time; wherein the object location module computing device and the object association module computing device are part of a location determining module computing device; the location determining module computing device is coupled to a network;
   receiving, at a network connected element, the data provided by the object identifier device;
   transmitting, from the network connected element, a signal containing the data and
   receiving, at the location determining module computing device, the signal from the network connected element;
   preventing false associations, at the object association module computing device, comprising a first locale, a second locale, a time spent in the first locale, and a time spent in the second locale, wherein if the time spent in the first locale is greater than or equal to a false association threshold time and the time spent in the second locale is less than the false association threshold time, association with the second locale is prevented and only an association with the first locale is made, whereby a false association determination is prevented; and
   disassociating, at the location determining module computing device, the association between the object and the second object and the object and the locale upon termination of a signal from the object identifier device for the location determined by the object location module computing device;
   whereby the association determination and the disassociation are established without input device triggering.

21. The method of claim 20, wherein the object identifier device comprises one or more of
   a transmitter configured to transmit a signal including the data identifying the object, a receiver configured to receive a signal requesting the data identifying the object; and a processor configured to control the transmitter and the receiver of the object identifier.

22. The method of claim 20, wherein the data identifying the object comprises a unique identifier.

23. The method of claim 20, wherein the data identifying the object is provided in a bar code on the object identifier or is magnetically encoded on the object identifier device.

24. The method of claim 20, wherein the object location module and the object association module are part of a location determining module.

25. The method of claim 24, wherein the location determining module further comprises one or more of a receiver configured to receive a signal from the object identifier device providing the data identifying the object, and a transmitter configured to transmit a request for data identifying the object.

26. The method of claim 20, wherein the object identifier device is a passive RFID device, and the network connected element is a passive RFID reader.

27. The method of claim 20, wherein the object identifier is a bar code, and the network connected element is a bar code reader.

28. The method of claim 20, wherein the location determining module is directly coupled to the object identifier device.

29. The method of claim 20, further comprising:
storing the object association at a storage device.

30. The method of claim 20, further comprising:
receiving, at a fixed location identifier, the data provided by the object identifier device;

transmitting, from the fixed location identifier, a signal containing the data; and receiving, at the object location module, the signal from the fixed location identifier.

31. The method of claim 20, wherein object identifier device is located in a health care facility.

32. The method of claim 20, wherein the locale comprises a room in the health care facility.

33. The method of claim 20, wherein the time period for determining an association depends on the type of object that the object identifier device is linked to.

34. The method of claim 20, wherein the time period for determining an association depends on the location or locale of the object identifier device.

35. The method of claim 20, wherein the time period for determining an association depends on the second object or locale the object identifier device is being associated with.

* * * * *